United States Patent
Burdick

(10) Patent No.: US 10,232,097 B2
(45) Date of Patent: Mar. 19, 2019

(54) VACUUM WOUND DEVICE

(71) Applicant: Steven Burdick, Dallas, TX (US)

(72) Inventor: Steven Burdick, Dallas, TX (US)

( * ) Notice: Subject to any disclaimer, the term of this patent is extended or adjusted under 35 U.S.C. 154(b) by 417 days.

(21) Appl. No.: 14/695,755

(22) Filed: Apr. 24, 2015

(65) Prior Publication Data

US 2015/0306287 A1    Oct. 29, 2015

Related U.S. Application Data

(60) Provisional application No. 61/984,238, filed on Apr. 25, 2014.

(51) Int. Cl.
*A61F 13/00* (2006.01)
*A61M 1/00* (2006.01)
*A61B 1/00* (2006.01)

(52) U.S. Cl.
CPC ..... *A61M 1/0086* (2014.02); *A61F 13/00042* (2013.01); *A61F 13/00068* (2013.01); *A61M 1/0088* (2013.01); *A61B 1/00* (2013.01); *A61M 1/0025* (2014.02); *A61M 2210/105* (2013.01)

(58) Field of Classification Search
CPC ........ A61F 13/00042; A61F 13/00068; A61M 1/0086; A61M 1/0088
See application file for complete search history.

(56) References Cited

U.S. PATENT DOCUMENTS

| | | | | |
|---|---|---|---|---|
| 5,374,261 A | * | 12/1994 | Yoon | A61B 17/00234 604/11 |
| 7,438,714 B2 | * | 10/2008 | Phan | A61B 18/1492 606/41 |
| 2001/0031943 A1 | * | 10/2001 | Urie | A61M 1/0088 604/43 |
| 2013/0023840 A1 | * | 1/2013 | Loske | A61M 1/0084 604/319 |
| 2013/0110066 A1 | * | 5/2013 | Sharma | A61L 24/0015 604/369 |

\* cited by examiner

*Primary Examiner* — Kai Weng
(74) *Attorney, Agent, or Firm* — Braxton Perrone, PLLC

(57) ABSTRACT

A system and method for a vacuum wound device. The system includes a wound vacuum device. The vacuum device includes a compressible sponge, vacuum tubing, and a delivery tube sized to house the wound vacuum device. The wound vacuum device is connected to a vacuum pump which creates and delivers the vacuum.

14 Claims, 4 Drawing Sheets

VACUUM WOUND DEVICE

PRIORITY

This application claims priority to provisional application 61/984,238 filed Apr. 25, 2014, the entirety of which is incorporate herein by reference.

BACKGROUND OF THE INVENTION

Technical Field

The present invention relates to a system and method for vacuum wound therapy.

Description of Related Art

Esophageal perforations are a life-threatening conditions which experiences a 13.2% mortality rate. The process begins with an inflammatory response to a mediastinal contamination. Without effective drainage it can progress to sepsis and septic shock. Surgery is the typical treatment, but the high mortality rate often persists. Stents have been attempted, but these suffer from many disadvantages. Consequently, there is a need for device and method of closing and treating these perforations and other defects absent surgery.

BRIEF DESCRIPTION OF THE DRAWINGS

The novel features believed characteristic of the invention are set forth in the appended claims. The invention itself, however, as well as a preferred mode of use, further objectives and advantages thereof, will be best understood by reference to the following detailed description of illustrative embodiments when read in conjunction with the accompanying drawings, wherein:

DETAILED DESCRIPTION

Several embodiments of Applicant's invention will now be described with reference to the drawings. Unless otherwise noted, like elements will be identified by identical numbers throughout all figures. The invention illustratively disclosed herein suitably may be practiced in the absence of any element which is not specifically disclosed herein.

Wound vacuum therapy has been utilized for closure of defects on surface areas. The application of such has been limited inside the body. The utilization of such a technique is hampered by the availability of devices to perform the technique.

Wound closure relies upon the migration of epithelial and subcutaneous tissue to the wound. If, however, the wound is infected or too large, a zone of stasis forms and prevents the migration of this critical tissue, and consequently, prevents closure of the wound. Sutures or staples are often used to close wounds. Such mechanical tools offer tension on the tissue and generally result in increased tissue migration to help close the wound. However, sutures or staples often damage the tissue. Further, some wounds are so infected or inflamed, that closure via sutures or staples is impossible. Finally, utilizing sutures or staples requires surgery, which many patients are often too ill to survive. A wound vacuum device overcomes many of these problems associated with sutures or staples.

A wound vacuum device, as used herein, is a device which can be used to treat wounds inside the body by applying a localized vacuum. A wound vacuum device, in one embodiment, removes excess fluid and bacterial, promotes blood flow to the desired tissue, and stimulates cells and cell growth. The wound vacuum device is connected to a vacuum pump which creates and delivers the vacuum. In one embodiment, high vacuum suction with construction of an endoscopic sponge, vacuum tubing, and suture is utilized.

Endoluminal vacuum therapy, utilizing a wound vacuum device, improves healing by removing infected secretions, reducing edema, increasing local perfusion, and promoting granulations tissue formulation. The results thus far demonstrate that this therapy has successfully closed esophageal perforations and leaks and done so while achieving low mortality rates. Vacuum therapy is a cavity focused treatment method. In one embodiment, the goal is to achieve complete closure of the cavity. Defect closure, in one embodiment, is the byproduct of a successfully closed cavity. In one embodiment, the placement can comprise either extraluminal placement, intraluminal placement, or combinations thereof. In one embodiment intraluminal placement is ideal for small cavities with little depth.

Figure 1:
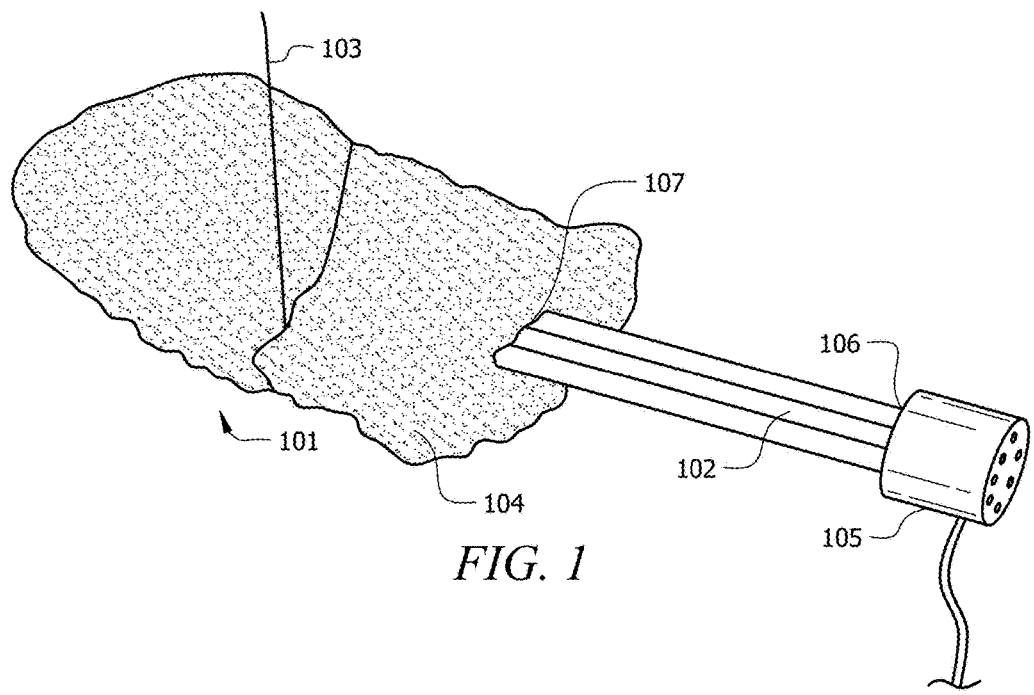
FIG. 1 is a top view of the components in one embodiment.

FIG. 1 is a top view of the components in one embodiment. FIG. 1 shows the sponge 101, which is utilized in the wound vacuum device. A sponge 101, as used herein, is a porous device which delivers a vacuum within the body and provides a mechanism which heals internal wounds. In one embodiment the sponge 101 comprises a non-rigid and compressible material. A compressible material is a material whose outside diameter can be easily decreased with minimal force. A common household sponge, for example, is a compressible material. Likewise, metallic frames made from materials such as Nitinol, which comprise a memory material and a set shape, are compressible. The sponge 101 material can comprise foam, gauze, metallic structures, etc. In one embodiment the sponge 101 comprises a hydrophilic foam that induces granulation tissue. In one embodiment the sponge 101 comprises Granufoam™ manufactured by Kinetic Concepts Inc. of San Antonio, Tex.

In one embodiment the sponge 101 comprises antibacterial, antibiotics, and/or antifungal properties. In another embodiment, the sponge 101 comprises a hemostatic material. In still other embodiments the sponge 101 comprises chemotherapy agents. The additional agents, such as the hemostatic material or the antibacterial can be coated, implanted, or otherwise incorporated into the sponge 101. Further, the sponge 101 can be manufactured from these materials.

In other embodiments the sponge 101 comprises a collagen, such as a natural collagen. Examples of a collagen include smooth muscle, basement membrane, lamina propria from human, animal and synthetic sources, bio-engineered material, etc. In still other embodiments, the sponge 101 comprises a Cook Oasis wound matrix sold by Smith & Nephew PLC, London, United Kingdom. In still other embodiments the sponge 101 comprises an autolytic debridement material. For example, it can comprise an amorphous hydrogel which gently re-hydrates necrotic tissue, facilitating autolytic debridement while being able to loosen and absorb slough and exudate. Further, in some embodiments, the sponge 101 can comprise a silicone gel or a hydrocellular foam. The sponge 101, in some embodiments, can comprise natural strengthening cellulose fibers or gelling cellulose ethyl sulphonate fibers. Specifically, in one embodiment the sponge 101 comprises a material which is 20% natural strengthening cellulose fibers and 80% gelling cellulose ethyl sulphonate fibers. In another embodiment the sponge 101 comprises an acellular matrix. As above, the sponge 101 can be coated or otherwise incorporate these materials, or the sponge can be manufactured from these materials.

In one embodiment the sponge material can comprise a hydrophobic material. This material has applications in urology, for example. In some embodiments the sponge 101 can comprise a mixture of materials of the materials discussed herein. In other embodiments the sponge 101 can comprise a hydrophobic and/or a hydrophilic sponge 101.

As discussed, in one embodiment the sponge 101 comprises a hemostatic material. The material can comprise any material which offers hemostatic properties. In one embodiment the hemostatic material comprises XStat™ manufactured by RevMedx, Inc. of Wilsonville Oreg. In operation, the vacuum from the vacuum tube 102 connects and couples the sponge 101 to the bleeding site and provides some pressure to maintain the sponge 101 attached to the bleeding site until hemostasis begins.

In one embodiment the sponge 101 comprises an anchoring device or other anti-migration device which helps keep the sponge 101 in the desired location. An anchoring device is any device known in the art to keep an object, such as a stent, lodged in a specified location within a body. These include hooks, areas of increased surface area, stents, etc. Those skilled in the art will understand the various tools and mechanism which can be utilized on or with the sponge 101 to prevent migration of the sponge 101. Further, in one embodiment, the sponge 101 can be used in conjunction with a stent for closure and wound healing. The stent can offer anti-migration benefits The sponge 101 can comprise virtually any desired shape and size, depending upon the application. The sponge can range from about ¼ of an inch to several inches in length. In one embodiment the sponge 101 comprises an oblong shape and is about 7 cm in length and about 2 cm wide. The shape of the sponge 101 will depend upon the application. For example, in one embodiment the sponge 101 comprises a Y-shape. In one such embodiment one upper tip of the "Y" is placed within the lumen of the GI tract, the other upper tip of the "Y" is placed into the perforation, and the suction port location on the section within the GI tract. In one embodiment the sponge 101 is used in the esophagus and measures 10 cm by 3 cm. IN one embodiment in the GI, the sponge is about 7 cm by about 2.5 cm. This description is provided only to illustrate the benefits of various shapes, and should not be deemed limiting.

In one embodiment, and as depicted, the sponge 101 is a porous material. The porosity allows the sponge 101 to spread the vacuum across the surface area of the sponge, decreasing the concentration of a vacuum at a single point. The porous sponge 101 also offers increased surface area upon which blood cells and other cells can adhere and coagulate, healing the wound. Further, the sponge 101 acts as a filter. Smaller objects and fluid are allowed to pass, being sucked in by the vacuum and removed through the vacuum tubing 102. In one embodiment, the porous nature of the sponge 101 allows lavage to dislodge it from the lumen of the body cavity. The porous nature of the sponge can be used for therapy with instillation of various medications, as discussed herein.

As depicted, the sponge 101 comprises two lobes 104 separated by a suture 103. As those skilled in the art will understand, the shape of sponge 101 can be controlled by placement of the suture or other tube coupling device 103.

Returning back to FIG. 1, coupled to the sponge 101 is the vacuum tubing 102. The vacuum tubing 102 can comprise any medical grade, hollow, tubing which can withstand a vacuum. In one embodiment, the vacuum tubing 102 comprises a nasogastric ("NG") tube. An NG tube is a tube which is generally inserted through the mouth or nose and placed into the desired location, for example, the esophagus or the stomach.

The vacuum tubing 102 can comprise any suitable material. In one embodiment, the vacuum tubing 102 comprises plastic. The outer diameter of the tubing can vary according to the application. In one embodiment the vacuum tubing 102 comprises a gauge between about 6 and 30. In one embodiment the vacuum tubing 102 comprises a 16 gauge. In one embodiment a 10 french and 16 tubing for the connection is utilized.

The vacuum tubing 102 has a first end 107 and a second end 106. The first end 107 is coupled, either directly or indirectly, to the sponge 101, and the second end 106 is coupled, either directly or indirectly, to the vacuum pump 105. In use the first end 107 is downstream from the second end 106. As used herein, upstream and downstream refer to relative locations with downstream being a point closer to the wound and upstream being a point closer to the vacuum pump 105. Thus, in operation the sponge 101 is downstream of the vacuum pump 105, and the vacuum pump 105 is upstream of the sponge 101. In one embodiment the vacuum tubing 102 is directly coupled to a vacuum pump 105. In other embodiments, however, the vacuum tubing 102 is not directly coupled to a vacuum pump 105. In one embodiment wherein the vacuum tubing 102 comprises an NG tube, the NG tube is further coupled at its upstream end to another tube, and that tube is couple to the vacuum pump 105. In some embodiments, wherein the NG tube is directly coupled to the vacuum pump 105, the vacuum pump 105 reads incorrect pressures resulting in false alarms, such as false lost suction alarms. An intermediate tubing, in some embodiments, reduces these false alarms.

Returning back to FIG. 1, coupling the sponge 101 to the vacuum tubing 102 is the tube coupling device 103. The tube coupling device 103 is any device which couples the vacuum tubing 102 with the sponge 101. The tube coupling device 103 can comprise sutures, wires, thread, clamps, magnets, etc. In one embodiment the tube coupling device 103 comprises a material that rotates and locks in place. The tube coupling device 103 can comprise virtually any material, including but not limited to, metal, plastic, rubber, etc. In one embodiment, and as depicted, the tube coupling device 103 comprises sutures which are sewn through both the vacuum tubing 102 and the sponge 101.

Figure 2:
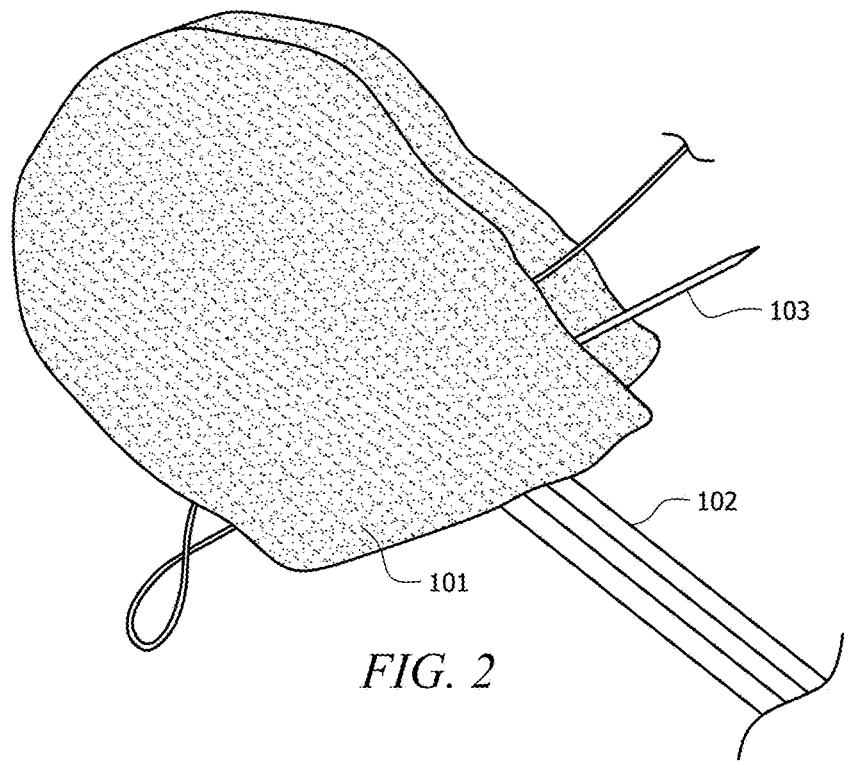
FIG. 2 is a perspective view of the sponge being coupled to the vacuum tubing via sutures in one embodiment.

FIG. 2 is a perspective view of the sponge 101 being coupled to the vacuum tubing 102 via sutures in one embodiment. The first end 107 of vacuum tubing 102, in one embodiment, is first placed within the sponge 101. In one embodiment, the tubing 102 simply pierces the sponge 101 and is placed approximately in the middle of the sponge 101. Thereafter, the sponge 101 is physically coupled to the tubing 102. As depicted, sutures are used as the tubing coupling device 103 to couple the sponge 101 to the vacuum tubing 102. In one embodiment, sutures pierce the vacuum tubing 102 at least one time, and in some embodiments, two or more times. The sutures are sewn through the sponge 101 to physically couple the sponge 101 to the vacuum tubing 102. Thereafter, the ends of the sutures are tied, cut, or otherwise secured.

Returning back to FIG. 1, FIG. 1 depicts a vacuum pump 105. A vacuum pump 105, as used herein, refers to any device which can create and supply a vacuum. A vacuum is any pressure below atmospheric pressure. Virtually any negative pressure (vacuum) can be utilized with the wound vacuum device. In one embodiment the vacuum pump 105 is capable of achieving pressures of between about 0.01 to 0.99 atmospheres. In one embodiment a continuous high negative suction is utilized. The negative pressure, in one embodiment, is maintained at between about 125 and about 175 mmHg.

Figure 3:
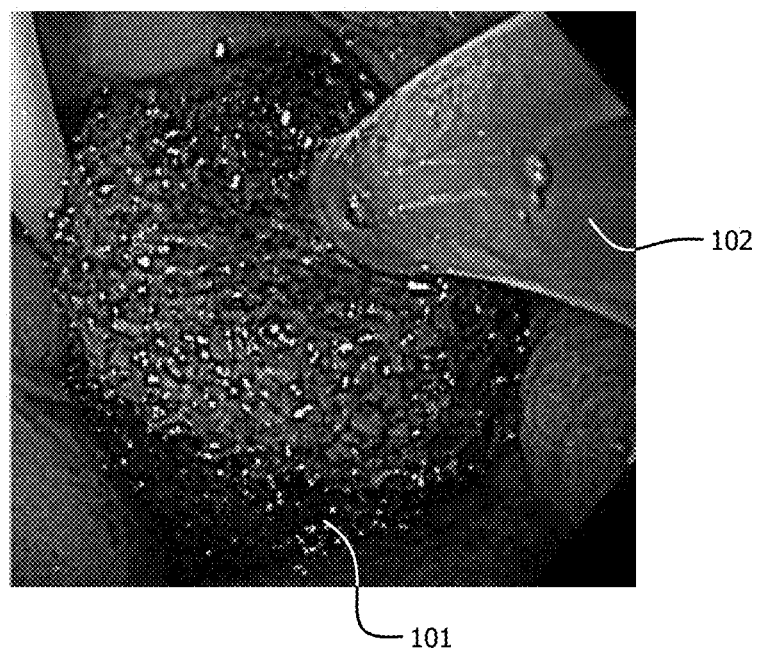
FIG. 3 is a top perspective view of a sponge deployed in the human body.

FIG. 3 is a top perspective view of a sponge deployed in the human body. As can be seen, the sponge 101 is deployed into the wound such that it is adjacent to tissue. The vacuum tube 102 is coupled to the sponge 101 as well as the vacuum pump 105 (not depicted). Thus, the vacuum tubing 102 is delivering a negative pressure to the wound. The negative pressure pulls adjacent tissue, such as epithelial and subcutaneous tissue, to the wound to help heal the wound. Further, the negative pressure pulls and removes bacterial and infectious materials, also aiding in the healing. Finally, the negative pressure promotes granulation tissue. Thus, the negative pressure aids in healing and closing of the wound.

The sponge 101 and vacuum tubing 102 are left in place for as long as necessary to heal the wound. In some embodiments, the sponges 101 are left in place where deployed for as little as less than a day to more than two weeks, depending upon the clinical situation. In one embodiment the sponges are changed every 3 to 7 days depending upon the clinical situation. In one embodiment changing the sponges every 3 to 4 days has been found to be the optimal time to promote healing. In some embodiments, exposure to secretions and fluids can cause buildup of material on and inside of the sponge sometimes leading to a reduction in suction or clogging. In one embodiment the sponge is changed on an on-demand basis during the acute infectious period. To monitor when the sponge needs changing, in one embodiment procalcitonin (PCT) levels are drawn to provide an early indicator of responses. In one embodiment, the sizes of subsequent replacement sponges 101 are modified to account for wound contraction. In some embodiments, as the wound begins to contract, successively smaller sponges 101 are used. This aids in closing the defect.

Endoscopic placement of wound vacuum devices as constructed by hand are often difficult to use and potentially complicated by the need for luminal visualization with air insufflation, blind insertions, and size of luminal constraints. Disrupted viscera i.e. perforations or fistulas are subject to air leakage with luminal insufflation during endoscopy which can cause serious life threatening complications including air embolus and cardiac tamponade. The insertion of the sponge without compression requires blind insertion with either the endoscope or overtube which during placement can cause perforation, tears with bleeding or other mechanical complications. The utilization of the device with blind insertions is often dangerous and technically challenging. Further complications include to air leakage and mechanical complications. Consequently, the lack of a delivery system is a deterrent for its utilization.

Figure 4:
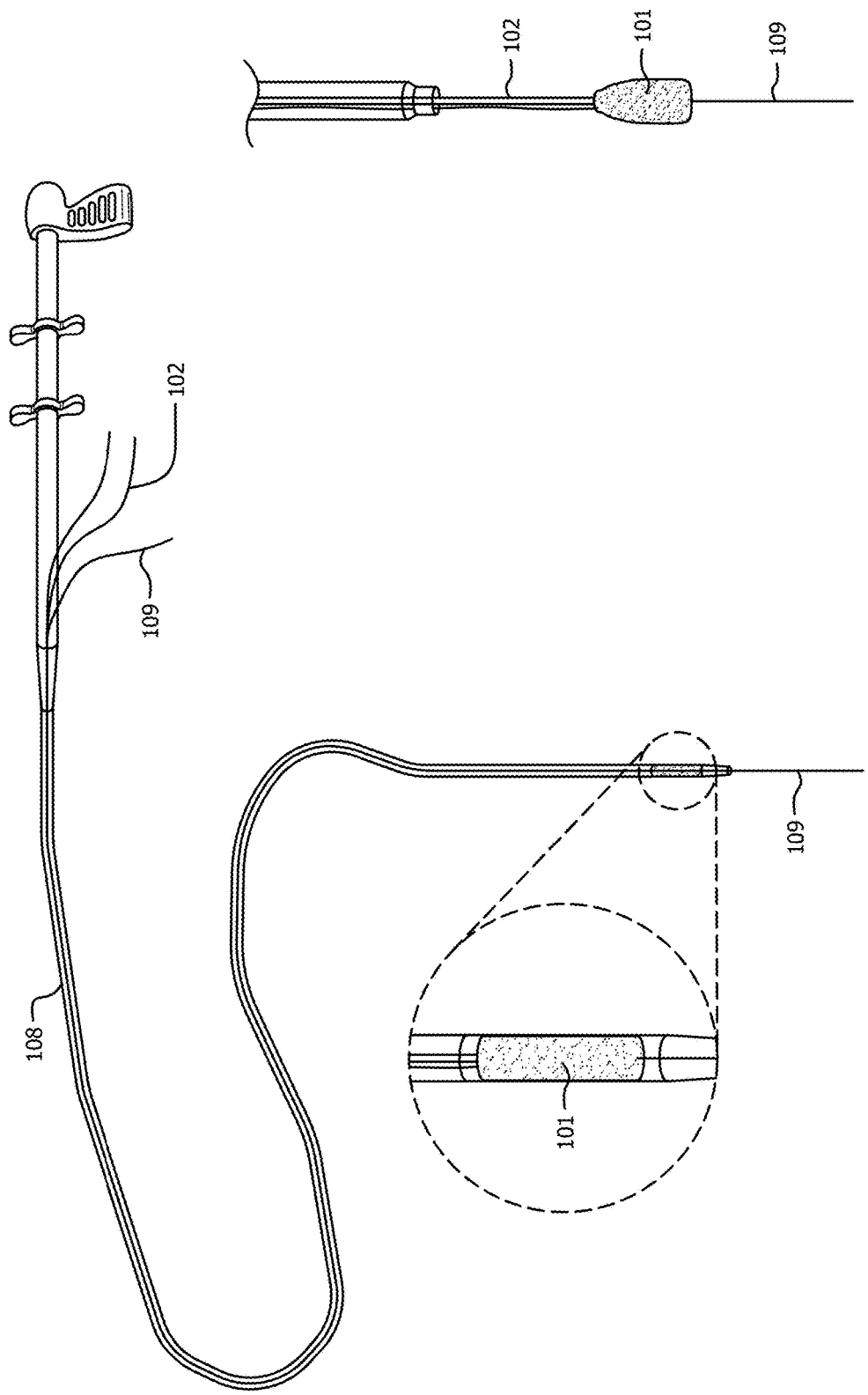
FIG. 4A is a schematic of a delivery stem with the sponge in the delivery position in one embodiment.
FIG. 4B is a schematic of a delivery system with the sponge in the deployed position one embodiment.

FIG. 4A is a schematic of a delivery system with the sponge in the delivery position in one embodiment. FIG. 4B is a schematic of a delivery system with the sponge in the deployed position in one embodiment. Turning to FIG. 4A, in one embodiment the delivery system compresses the sponge 101 within a catheter 108. The catheter 108 can comprise any delivery tube which comprises a diameter greater than the diameter of the vacuum tubing 102. As depicted the catheter 108 houses the compressed sponge 101, the vacuum tube 102, and the guide wire 109. The sponge compression allows a smaller diameter catheter 108 to be positioned for deployment than if the sponge 101 were not compressed.

The guide wire 109 can comprise any guide wire known in the art. The operator uses the guide wire 109 to control and direct the placement of the sponge 101. At the desired location, the catheter 108 is withdrawn, and the sponge 101 is allowed to expand. FIG. 4B shows the expanded sponge 101 with the catheter 108 removed.

In one embodiment the sponge 101, vacuum tubes 102, and/or the guide wire 109 comprise markers. Markers allow the operator to determine the location of the delivery system within the body. Those skilled in the art will understand the various markers that can be utilized.

There are several benefits in using a system such as that depicted in FIGS. 4A and 4B. First, the guide wire 109 allows the operator to better control and deliver the sponge 101 compared to blind insertion. Second, as noted above, the use of a catheter 108 or other such sheath allows for a more compact delivery mechanism. This allows the sponge 108 to be utilized in smaller spaces and channels than using an uncompressed sponge.

While one embodiment has been discussed wherein the sponge 101 expands upon removal of the catheter 108, this is for illustrative purposes only and should not be deemed limiting. There are several release mechanism including a covering sheath with exposure of the sponge by utilization of either a plunger device to expose the sponge or withdrawing the sheath over the sponge so that it would become free, or removal of a covering wrap. For example, in one embodiment the sponge 101 is restricted by a string which is wound about the sponge 101 to constrain the sponge 101. When the string is removed, the sponge 101 can expand.

Figure 5:
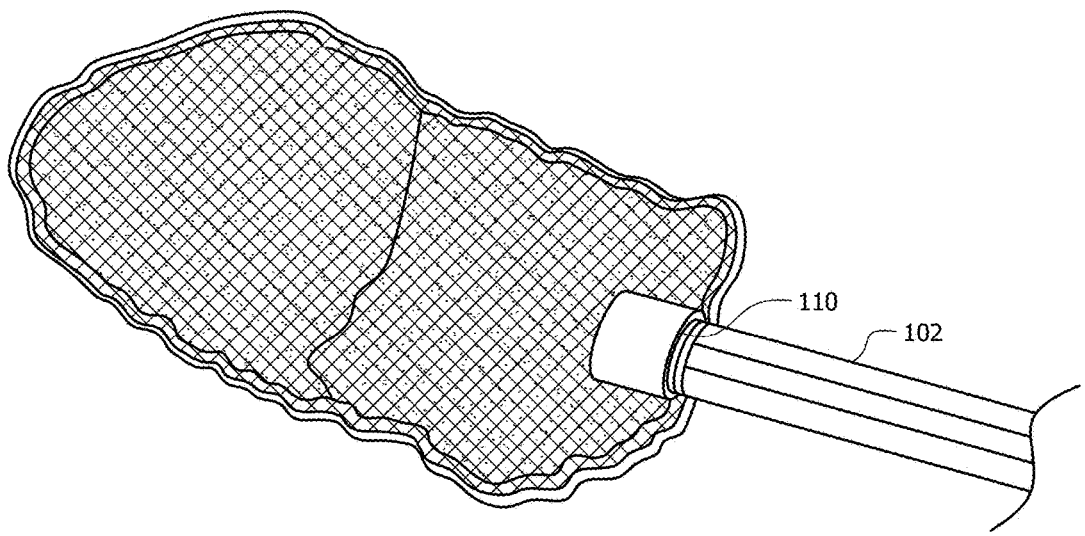
FIG. 5 is a top view of an embodiment utilizing a net.

FIG. 5 is a top view of an embodiment utilizing a net. Another alternative for deployment and/or recapture includes a web-like net 111 that can be pulled like a draw string to capture the sponge 101 for delivery and released within the lumen. The net 111 can comprise virtually any medical grade material which encompasses the sponge 101. When pulled, the net 11 pulls and directs the sponge 101. If the net 111, for example, is pulled within a catheter 108, then the sponge 101 will compress within the catheter 108. Likewise, if the catheter 108 is removed, the sponge 101 will assume the uncompressed state.

As depicted in FIG. 5, the sponge 101 comprises an attaching mechanism 110. The attaching mechanism 110 can be coupled to the sponge 101 directly, or the attaching mechanism 110 can be attached via the net 111. An attaching mechanism 110 is a device which allows the sponge 101 to be attached to a delivery and/or removal system. The attaching mechanism 110 can comprise threading, snaps, or other mechanism features which allow the coupling of two objects. As one, non-limiting example, consider the delivery system of FIG. 4 utilizing a catheter 108 and a guide wire 109. In such an embodiment, once deployed, the guide wire 109 can be attached to the sponge 101 via the attaching mechanism 110. Accordingly, the catheter 108 and/or the guide wire 109 can be removed while leaving the sponge 101 and the vacuum tubing 102 in place. When the sponge 101 is to be removed, the guide wire 109, for example, can couple to the attaching mechanism 110, and pull the sponge 101 to the compressed position within the catheter 108.

As noted, the delivery system can be placed over a wire or freely passed depending on the location of therapy intended. The vacuum tubing 102 can be routed per nasal or per other created ostomy depending on the location and nature of the malady. Further, in one embodiment, multiple small lumens within the tubing 102 would allow for sensing, monitoring, installation of medications, and optical viewing.

As noted, there are several methods to deploy and remove the vacuum wound device. In one embodiment it is deployed without the use of endoscopy. In another embodiment the wound vacuum device is placed alongside the endoscope with a release mechanism. In still other embodiments the wound vacuum device 101 is placed through a working channel in the endoscope over a wire or freely into the wound. Other techniques include over the scope attachment, through the scope, guidewire stent scope withdrawn, an NG tube, and other deployment methods known in the art. In one embodiment a piggyback method is utilized whereby the suture is grabbed with forceps and directed to the desired location. In one such piggyback method, an additional suture forms a loop at one end of the sponge. The loop of the suture is grasped and guided with a device such as an endoscope. In still another embodiment the tube is grabbed with forceps a few centimeters behind the sponge. This allows the sponge to flex backwards on itself. Such a method has an advantage in that it increases the visualization available to the user. In another embodiment a rendezvous method is utilized. In this method, an open ended drain is accessible with an endoscopic or gastronomic tube. First place the endoscopic forceps down, through, and out of the drain or gastronomic tube, under endoscopic visualization. Next, grab the forceps with another pair of endoscopic forceps placed through the scope. Next, interlock each jaw in the closed position. Once the forceps are secured, the scope can then be withdrawn through the mouth. Now, the sponge 101 is ready to be pulled into place. In one embodiment, a suture placed at the end of the sponge 101 helps allow the sponge 101 to be pulled into the desired location. In one embodiment the sponge is placed via percutaneous insertion.

Figure 6:
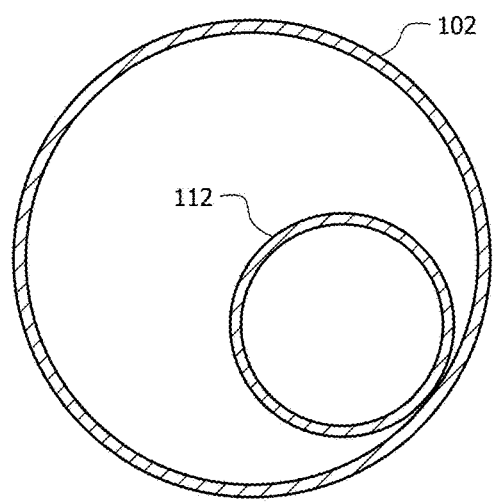
FIG. 6 is a cross-sectional view of a vacuum tubing with an internal supplemental tube.

FIG. 6 is a cross-sectional view of a vacuum tubing with an internal supplemental tube. A supplemental tube 112 is an additional tube which travels parallel with the vacuum tubing 102 which is used to deliver or remove a substance. The supplemental tube 112 can be located within the vacuum tubing 102 as illustrated, or the vacuum tubing 102 can be located within the supplemental tube 112. Referring to FIG. 6, in one embodiment, and as illustrated, the vacuum tubing 102 comprises one or more supplemental tubes 112. As depicted, the supplemental tube 112 fits within the vacuum tubing 102. The supplemental tube 112 can be used to delivery substances such as a saline flush, chemotherapy drugs, medicinal fluids or gels, medicines, antibacterial agents, etc. In operation, the vacuum tubing 102 provides the suction and the supplemental tube 112 simultaneously provides the substance to the wound. Thus, the supplemental tube 112 can be used to supply fluids to wash and flush the wound. In one embodiment, the same fluids or substance supplied by the supplemental tube 112 can then be removed and withdrawn by the vacuum tubing 102. In one embodiment the fluid or substance being supplied by the supplemental tube 112 travels in the opposite direction from the fluid being withdrawn by the vacuum tubing 102. In still other embodiments the supplemental tube 112 can house sensing devices for bacterial, blood, optics, sensors, medications, etc.

The wound vacuum device described herein can be used to close wounds located throughout the body. The wound vacuum device can be used to heal wounds located in in gastrointestinal tract ("GI tract") and other organs. For example, the wound vacuum device can be used for fistulas and perforation of the esophagus, stomach, and duodenum (small intestines), as well as colonic applications. In one embodiment the device is a remedy for bariatric surgery complications. In still another embodiment the device is utilized on devastating injuries where the patients are too ill to survive surgery. In still other embodiments the device is used in other maladies including bladder fistula and pancreas. In still other embodiments the device us used in the abdomen, pelvis, chest, urology, gyn, and other orthopedic and drain applications.

The wound vacuum device described herein can also function as a drain. A drain is used to remove fluids such as pus, blood, or other fluids, away from a surgical site. Use of the device as a drain is similar to the use described above. The sponge 101 acts as a filter which allows smaller objects and fluids to be withdrawn into the vacuum and removed via the vacuum tubing 102. Because the sponge 101, in one embodiment, acts as a filter, and due, in part, to the increased surface area, plugging of the sponge 101 is reduced compared to prior art drains. The sponge 101 prevents larger items, which could potentially clog or plug the vacuum tubing 102, from reaching the vacuum tubing 102. Further, in one embodiment the open cell structure of the sponge 101 provides increased suction distribution over a larger surface area when compared to traditional draining methods and devices. By providing continuous effective draining, the device and method discussed herein has a distinct advantage over traditional draining methods and devices in its ability to remove the septic focus.

The sponge 101 can be used to function as a drain in virtually any circumstance where a drain would typically be utilized. These include, but are not limited to, GI, chest, abdomen, other such orthopedics, etc. When used as a drain, the sponge 101 can be delivered and recaptured using virtually any of the methods or devices discussed herein.

As noted, the device can be used to close a variety of defects and perforations. One embodiment will now be discussed with regards to an esophageal perforation. This is for illustrative purposes only and should not be deemed limiting.

In this embodiment the therapy was performed under general endotracheal anesthesia. In other embodiments other types of anesthesia, including regional blocks and sedation can be used. In still other embodiments, no anesthesia is used. First the cavity is assed to determine the size of the defect. Any structures with the cavity are identified, as are any problematic drainage areas which could not be drained with vacuum therapy alone. In some embodiments, a CT scan can be used. The presence of necrosis is also checked. Next, the cavity is irrigated, and debrided, if necessary, using methods and devices known in the art. Thereafter, a vacuum tube 102, such as an NG tube, is placed down through the nose and back out through the mouth. The sponge is then secured to the NG tube using methods and devices discussed herein. In one embodiment, a tunnel within the sponge is created to provide space for the NG tube. This tunneling can be created by cutting or otherwise removing sponge in the area of the tunnel. In other embodiments the tunnel is created by forcing the NG tube through the sponge. In one embodiment, all drain holes in the NG tube are covered by the sponge. This helps prevent direct suctioning of tissue. It further helps reduce blockage. In one embodiment, to prevent the sponge from being dislodged once placed, a vacuum is applied to the NG tube prior to removing the endoscope.

Treatment with the sponge, in combination with irrigation, and debridement can result in immediate reduction in the inflammatory response. In one embodiment, the goal of the vacuum therapy is to achieve complete closure of the cavity. In one embodiment, complete closure refers to cavities which were 1 cm or less in depth, which illustrated good granulation tissue, and which appeared sealed on endoscopic examination. The complete closure is achieved through a combination of wound contraction, otherwise known as a cavity collapse, as well as granulations formation.

The sponge can be removed by a variety of methods and devices. In one embodiment the sponge is removed by reversing the steps in which it was inserted. In one embodiment the sponge is removed via an endoscope. The sponge is first flushed with saline through the NG tube. Thereafter, either the NG tube or the suture is grabbed with forceps, such as rat tooth forceps, and is pulled out of the mouth. In one embodiment the forceps were used to grab the NG tube 1-2 cm behind the sponge. This allows the sponge to retroflex backward allowing for better visualization. In other embodiments a sutured loop was attached to the end of the NG tube and grasped, and the sponge was guided down inline with the endoscope.

While the invention has been particularly shown and described with reference to a preferred embodiment, it will be understood by those skilled in the art that various changes in form and detail may be made therein without departing from the spirit and scope of the invention.

DETAILED DESCRIPTION

The following clauses are offered as further description of the disclosed invention.

Clause 1. A wound vacuum device comprising:
a compressible sponge;
vacuum tubing comprising a first end and a second end, wherein said first end is coupled to said sponge via a tube coupling device;
wherein said first end of said vacuum tubing is fully encompassed by said sponge.

Clause 2. The wound vacuum device of any proceeding or preceding claim wherein said second end of vacuum tubing is coupled to a vacuum pump.

Clause 3. The wound vacuum device of any proceeding or preceding claim wherein said sponge further comprises an anchoring device.

Clause 4. The wound vacuum device of any proceeding or preceding claim further comprising a net, wherein said net fully encompasses said sponge, and wherein said net further comprises an attaching mechanism.

Clause 5. The wound vacuum device of any proceeding or preceding claim wherein said vacuum tubing comprises a supplemental tube.

Clause 6. The wound vacuum device of any proceeding or preceding claim wherein said supplemental tube is located within said vacuum tubing.

Clause 7. The wound vacuum device of any proceeding or preceding claim wherein said compressible sponge comprises a Y-shape.

Clause 8. The wound vacuum device of any proceeding or preceding claim wherein said sponge comprises a porous material.

Clause 9. The wound vacuum device of any proceeding or preceding claim wherein said sponge comprises an oblong shape.

Clause 10. A system for use in wound vacuum therapy, said system comprising:
a wound vacuum device comprising:
a compressible sponge;
vacuum tubing comprising a first end and a second end, wherein said first end is coupled to said sponge via a tube coupling device;
wherein said first end of said vacuum tubing is fully encompassed by said sponge.
a delivery tube, wherein the delivery tube is sized so as to house the wound vacuum device.

Clause 11. The system of claim 10 further comprising a guide wire.

Clause 12. The system of any proceeding or preceding claim further comprising an attaching mechanism which couples the wound vacuum device to the guide wire.

Clause 13 The system of any proceeding or preceding claim wherein said wound vacuum device further comprises a net which fully encompasses said sponge.

Clause 14. The system of any proceeding or preceding claim wherein said net further comprises an attaching mechanism.

Clause 15. The system of any proceeding or preceding claim wherein said vacuum tubing comprises a supplemental tube located within said vacuum tubing.

Clause 16. The system of any proceeding or preceding claim wherein said supplemental tube houses a sensing device.

Clause 17. The system of any proceeding or preceding claim wherein a fluid is pumped toward said wound vacuum device through said supplemental tube.

Clause 18. The system of any proceeding or preceding claim further comprising markers.

I claim:

1. A wound vacuum device comprising:
a compressible sponge;
vacuum tubing comprising a first end and a second end, wherein said first end is coupled to said sponge via a tube coupling device;
wherein said first end of said vacuum tubing is fully encompassed by said sponge;
a delivery tube, wherein the delivery tube is sized so as to house the wound vacuum device and wherein said compressible sponge is configured to be placed inside a human body to heal internal wounds;
a net, wherein said net fully encompasses said sponge, and wherein said net further comprises an attaching mechanism;
wherein said sponge comprises a porous material and wherein said sponge comprises two lobes separated by suture, wherein said suture is sewn through said sponge and said vacuum tubing.

2. The wound vacuum device of claim 1 wherein said second end of vacuum tubing is coupled to a vacuum pump.

3. The wound vacuum device of claim 1 wherein said sponge further comprises a guide wire.

4. The wound vacuum device of claim 1 wherein said vacuum tubing comprises a supplemental tube.

5. The wound vacuum device of claim 4 wherein said supplemental tube is located within said vacuum tubing.

6. The wound vacuum device of claim 1 wherein said compressible sponge comprises a Y-shape.

7. The wound vacuum device of claim 1 wherein said sponge comprises an oblong shape.

8. A system for use in wound vacuum therapy, said system comprising:
a wound vacuum device comprising:
a compressible sponge;

vacuum tubing comprising a first end and a second end, wherein said first end is coupled to said sponge via a tube coupling device;
wherein said first end of said vacuum tubing is fully encompassed by said sponge;
wherein said wound vacuum device further comprises a net which fully encompasses said sponge;
a delivery tube, wherein the delivery tube is sized so as to house the wound vacuum device and wherein said compressible sponge is configured to be placed inside a human body to heal internal wounds;
wherein said sponge comprises a porous material and wherein said sponge comprises two lobes separated by suture, wherein said suture is sewn through said sponge and said vacuum tubing.

9. The system of claim 8 further comprising an attaching mechanism which couples the wound vacuum device to a guide wire.

10. The system of claim 8 wherein said net further comprises an attaching mechanism.

11. The system of claim 8 wherein said vacuum tubing comprises a supplemental tube located within said vacuum tubing.

12. The system of claim 11 wherein said supplemental tube houses a sensing device.

13. The system of claim 11 wherein a fluid is pumped toward said wound vacuum device through said supplemental tube.

14. The system of claim 8 further comprising markers.

\* \* \* \* \*